United States Patent

Schürmann et al.

[11] Patent Number: 6,117,074
[45] Date of Patent: Sep. 12, 2000

[54] METHOD CONDUCTED IN A COMPUTER FOR CLASSIFICATION OF A TIME SERIES HAVING A PRESCRIBABLE NUMBER OF SAMPLES

[75] Inventors: Bernd Schürmann, Haimhausen; Gustavo Deco, München, both of Germany

[73] Assignee: Siemens Aktiengesellschaft, Munich, Germany

[21] Appl. No.: 09/142,237
[22] PCT Filed: Feb. 2, 1997
[86] PCT No.: PCT/DE97/00350
  § 371 Date: Sep. 3, 1998
  § 102(e) Date: Sep. 3, 1998
[87] PCT Pub. No.: WO97/33238
  PCT Pub. Date: Sep. 12, 1997

[30] Foreign Application Priority Data

Mar. 6, 1996 [DE] Germany ............... 196 08 733

[51] Int. Cl.$^7$ ...................................... A61B 5/00
[52] U.S. Cl. ............................................. 600/300
[58] Field of Search ............................ 600/300, 509, 600/518, 519

[56] References Cited

U.S. PATENT DOCUMENTS 5,792,062 8/1998 Poon et al. ..................... 600/509
5,938,594 8/1999 Poon et al. ..................... 600/300

OTHER PUBLICATIONS

"Komolexitätsanalyse in der Kardiologie," Morfill, Physikalische Blätter, vol. 50, No. 2, pp. 156–160, (1994).

Licox, GMS, Gesellschaft für Medizinische Sondentechnik mbH, Advance Tissue Monitoring.

"Learning Time Series Evolution by Unsupervised Extraction of Correlations," Deco et al., Physical Revue E. vol. 51, No. 3, pp. 1780–1790 (Mar, 1995).

"Time Series Analysis of Complex Dynamics in Physiology and Medicine," Glass et al., Medical Progress Through Technology, vol. 19, No. 3, pp. 115–128 (Jan., 1993).

*Primary Examiner*—Max Hindenburg
*Assistant Examiner*—Brian Szmal
*Attorney, Agent, or Firm*—Hill & Simpson

[57] ABSTRACT

In a computerized method for classification of a time series containing a prescribable number of samples, such as an electrical signal, a parameterized, dynamic set is determined in the computer from the samples in the time series, the set identifying non-linear correlations between the samples of the time series. A classification of the time series is implemented in the computer on the basis of the parameterized, dynamic multiplicity.

5 Claims, 2 Drawing Sheets

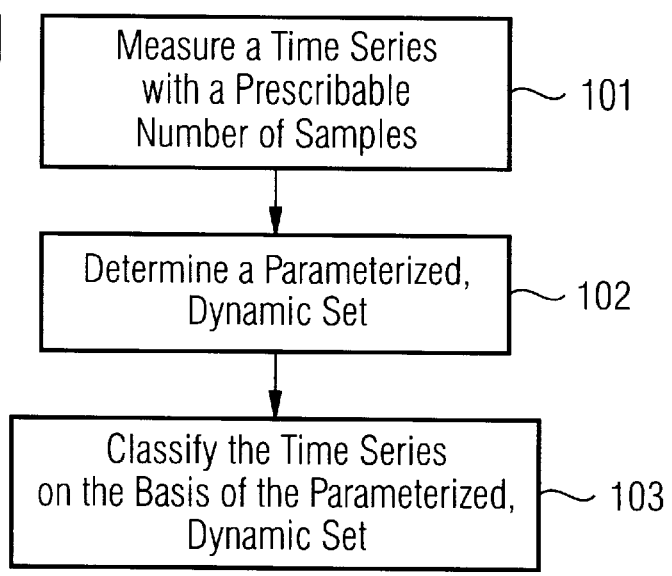
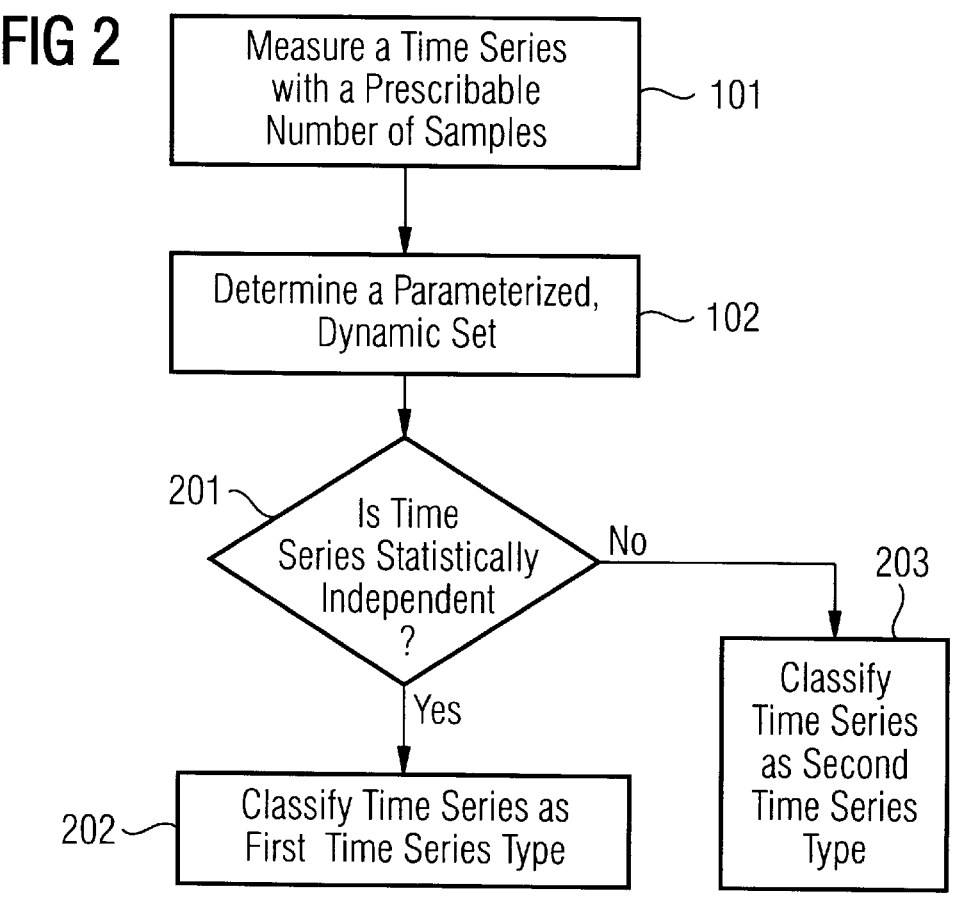

METHOD CONDUCTED IN A COMPUTER FOR CLASSIFICATION OF A TIME SERIES HAVING A PRESCRIBABLE NUMBER OF SAMPLES

BACKGROUND OF THE INVENTION

1. Field of the Invention

The present invention is directed to a computerized method for classifying a time series containing a prescribable number of samples, such as an electrical signal.

2. Description of the Prior Art

In many technical fields it is of interest to draw conclusions about the future behavior of the time series from measured time series. The prediction of the future "behavior" of the time series ensues given the assumption that the time series comprises nonlinear correlations or linear correlations (statistical dependencies) between the samples of the time series.

This problem also obtains to considerable significance in various medical fields, for example in cardiology. Specifically in the problem area of sudden cardiac death, it can be vital to recognize early warning signs of sudden cardiac death in order to initiate counter-measures against the occurrence of sudden cardiac death as early as possible.

It is known that a time series of an electrocardiogram that is not correlated describes a heart that is not at risk with respect to sudden cardiac death. A heart at risk with respect to sudden cardiac death is described by a time series of the electrocardiogram that comprises non-linear correlations between the samples of the time series G. Morfill, "Komplexitätsanalyse in der Kardiologie," Physikalische Blätter, Vol. 50, No. 2, pp. 156–160, (1994). It is also known from the Morfill article to determine time series of an electrocardiogram that describe hearts that are at risk with respect to sudden cardiac death from the graphic phase space presentation of two successive heartbeats.

LICOX, GMS, Gesellschaft für Medizinische Sondentecknik mbH, Advanced Tissue Monitoring discloses a method with which the time curve of the local oxygen voltage of the brain (tipO2) can be determined.

The method disclosed in the Morfill article exhibits all of the disadvantages that are typical of empirical methods. In particular, the error susceptibility of graphic interpretations by a human, the problem of setting a threshold from which a time series is classified as at risk, as well as imprecisions in the presentation of the Fourier transform on the picture screen are considered disadvantageous in the known method.

SUMMARY OF THE INVENTION

An object of the present invention is a method for analytically classifying a time series with the assistance of a computer.

The above object is achieved in accordance with the principles of the present invention in a method for classifying a time series that contains a prescribable number of samples, such as an electrical signal, employing a computer, wherein a parameterized, dynamic set is obtained in the computer from the samples, the set describing non-linear correlations between the samples of the time series, and wherein the time series is classified in the computer on the basis on the parameterized, dynamic set.

In the inventive method, a parameterized, dynamic multiplicity is determined for a time series that contains a prescribable plurality of samples. Non-linear correlations between the samples of the time row are described with the parameterized, dynamic multiplicity on the basis of parameters that indicate the form of the parameterized, dynamic multiplicity. A classification of the time series is implemented on the basis of the parameterized, dynamic multiplicity.

Compared to the known, empirical inventive method, the method has the particular advantage that no error sources arise due to imprecise evaluation of the results. An unambiguous, replicatable classification of the time series is achieved by the analytic procedure. A further advantage is in the substantially increased speed with which the entire process of classification is implemented.

To allow the method to be conducted more rapidly, it is advantageous in the classification to classify the time series only into a first time series type and a second time series type. A first time series type thereby describes a time series wherein a non-linear correlation is found between the samples, and the second time series type describes a time series that is statistically independent. The parameterized, dynamic multiplicity differs so greatly for these two time series types that a classification can be implemented very fast without greater calculating outlay.

DESCRIPTION OF THE DRAWINGS

FIG. 1 is a flowchart showing the basic steps of the inventive method.

FIG. 2 is a flowchart showing a variation of the inventive method wherein classification is made into only two time series types.

DESCRIPTION OF THE PREFERRED EMBODIMENTS

Figure 3:
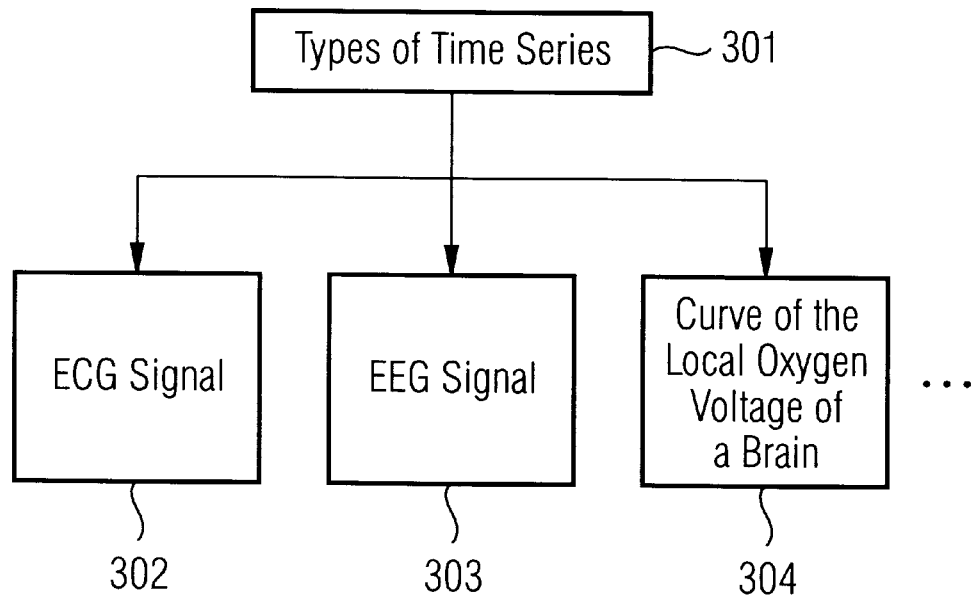
FIG. 3 is a block diagram showing various possibilities for the types of the time series.

FIG. 1 shows the method steps of the inventive method.

In a first step 101, a time series is measured, for example a time series in the form of an electrical signal. Since the classification of the time series is implemented with a computer R, the time series contains a prescribable number of samples, dependent on a sampling interval. When the measured signal that represents the time series is analog, then the signal must be sampled so that it can be processed with the computer R.

In a second step 102, a parameterized, dynamic set is determined for the time series. The determination of the parameterized, dynamic set ensues in such a way that non-linear correlations that the samples exhibit among one another are extracted. A method for the determination of the parameterized, dynamic set is known from the article "Learning Time Series Evolution by Unsupervised Extraction of Correlations," Deco et al., Physical Revue E, Vol. 51, No. 3, pp. 1780–1790 (March, 1995).

On the basis of this parameterized, dynamic set, it is now possible to make statements about potentially existing non-linear correlations between the samples.

In a last step 103, the time series is classified on the basis of the parameterized, dynamic set.

The method is particularly suited for employment in medical fields. In these fields, in particular, the early recognition of sudden cardiac death on the basis of electrocardiogram signals (ECG signals) is an important area of employment for the inventive method.

As described in the aforementioned Morfill article, a determination can be made on the basis of electrocardiogram signals as to whether the heart for which the electrocardiogram was measured is at risk with respect to sudden cardiac death. Hearts at risk with respect to sudden cardiac death are thereby characterized in the electrocardiogram signals by the presence of non-linear correlations between the samples of the electrocardiogram signal.

Hearts not at risk with respect to sudden cardiac death exhibit no correlations at all between the samples of the time series in the ECG signal, the signals are statistically independent of one another.

FIG. 2 shows a development of the inventive method with which the implementation of the method from the measurement of the time series up to the classification of the time series is conducted considerably faster. This is achieved by a simplified classification. The simplification is achieved by conducting a check as to whether the samples of the time series are statistically dependent on one another 201, this check being conducted only with reference to the parameterized, dynamic set. When this is the case, the time series is classified 202 as a first time series type. For the applied example of electrocardiogram signals in hearts at risk and not a risk with respect to sudden cardiac death, this classification corresponds to a classification of the electrocardiogram signal as a signal of a heart at risk since non-linear correlations between the samples of the time series, of the electrocardiogram signal in this case, are present in this case.

When the samples of the time series are statistically independent, however, the time series is classified 203 as a second time series type. In the above-described example for the electrocardiogram signal, this corresponds to a classification as a signal of a heart not at risk with respect to sudden cardiac death.

In an overview not to be interpreted as final, FIG. 3 indicates a few examples of possible types of time series for which the inventive method can be utilized 301:

electrocardiogram signals (ECG signals) 302;

electroencephalogram signals (EEG signals) 303;

signals that describe the curve of the local oxygen voltage of a brain 304.

A possibility of measuring a signal that describes the curve of the local oxygen voltage in a brain is presented in the aforementioned Advanced Tissue Monitoring reference.

The method, of course, can be utilized in all fields wherein a time series is to be classified on the basis of parameterized, dynamic multiplicities.

Figure 4:
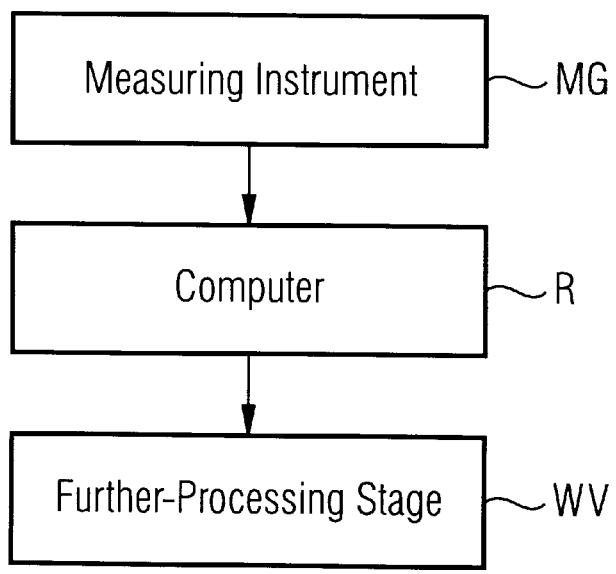
FIG. 4 is a block diagram showing the basic components of a computer system in which the inventive method can be implemented.

FIG. 4 shows the computer R with which the inventive method is necessarily implemented.

The computer R processes the time series registered by the measuring instrument MG and supplied to the computer R.

It is thereby of no significance whether the formation of the samples from the possibly analog signal is implemented in the measuring instrument MG or in the computer R. Both versions are provided for the inventive method.

The measuring instrument can, for example, be an electrocardiograph (ECG), an electroencephalograph (EEG) or an apparatus, too, that works according to the method presented in [2].

The classification result that was determined by the computer R in the above-described way is further-processed in a stage for further-processing WV and, for example, is displayed for a user. This stage WV can, for example, be a printer, a picture screen or a loudspeaker as well, via which an acoustic or visual signal is forwarded to a user.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for computerized classification of a time series containing a prescribable number of samples, comprising the steps of:

supplying a time series containing a prescribable plurality of samples to a computer and, in said computer, determining a parameterized, dynamic set from the samples in said time series identifying non-linear correlations between said samples of said time series; and classifying said time series in said computer dependent on said parameterized, dynamic set.

2. Method according to claim 1, wherein the time series is classified either into a first time series type or into a second time series type in the classification.

3. Method according to claim 1, wherein the time series comprises an electrocardiogram signal.

4. Method according to claim 1, wherein the time series comprises an electroencephalogram signal.

5. Method according to claim 1, wherein the time series comprises a signal describing a time curve of a local oxygen voltage of a brain.

* * * * *